United States Patent
Ciok et al.

(10) Patent No.: US 7,172,581 B2
(45) Date of Patent: Feb. 6, 2007

(54) OSTOMY APPLIANCE WITH A REMOVABLE, WASHABLE AND REUSABLE SEALING MEMBER

(75) Inventors: Danuta Ciok, Nivaa (DK); Michael Hansen, Gilleleje (DK)

(73) Assignee: Coloplast A/S, Humlebaek (DK)

( * ) Notice: Subject to any disclaimer, the term of this patent is extended or adjusted under 35 U.S.C. 154(b) by 102 days.

(21) Appl. No.: 10/489,250

(22) PCT Filed: Sep. 23, 2002

(86) PCT No.: PCT/DK02/00623

§ 371 (c)(1),
(2), (4) Date: Mar. 11, 2004

(87) PCT Pub. No.: WO03/026541

PCT Pub. Date: Apr. 3, 2003

(65) Prior Publication Data

US 2004/0260256 A1    Dec. 23, 2004

(30) Foreign Application Priority Data

Sep. 24, 2001    (DK) .................. PA 2001 01389

(51) Int. Cl.
*A61F 5/44*    (2006.01)
(52) U.S. Cl. ............ 604/339; 604/336; 604/341; 604/342; 604/344; 604/355
(58) Field of Classification Search .......... 604/277, 604/332–345, 355
See application file for complete search history.

(56) References Cited

U.S. PATENT DOCUMENTS

| | | | |
|---|---|---|---|
| 3,983,298 A | 9/1976 | Hahn et al. | |
| 4,367,732 A | 1/1983 | Poulsen et al. | |
| 4,838,253 A * | 6/1989 | Brassington et al. | 602/48 |
| 4,889,534 A * | 12/1989 | Mohiuddin et al. | 604/339 |
| 5,051,259 A | 9/1991 | Olsen et al. | |

(Continued)

FOREIGN PATENT DOCUMENTS

GB    2 290 974    1/1996

(Continued)

OTHER PUBLICATIONS

Lewis, Richard J. Sr., Hawley's Condensed Chemical Dictionary, 13th Edition, 1997, John Wiley & Sons, Inc., pp. 997.*

*Primary Examiner*—Tatyana Zalukaeva
*Assistant Examiner*—Michael G. Bogart
(74) *Attorney, Agent, or Firm*—Jacobson Holman PLLC

(57) ABSTRACT

An ostomy appliance including a body side member having an adhesive wafer for securing the appliance to the user's skin, and a separate sealing member for sealing against the stoma, the separate sealing member being in the form of a disc having a centre hole for accommodating the stoma. The disc is made from a material that may be detached, rinsed and reapplied such that the disc has a service time at least as long as the body side member. The disc reduces the frequency of stressing the skin around the stoma due to exchange of the body side member by protecting the surface of the adhesive wafer from soiling by and attack from the aggressive visceral contents and facilitates the cleaning of the body side member.

16 Claims, 1 Drawing Sheet

U.S. PATENT DOCUMENTS

| | | | |
|---|---|---|---|
| 5,074,852 A * | 12/1991 | Castellana et al. | 604/336 |
| 5,209,744 A * | 5/1993 | Abe et al. | 604/342 |
| 5,269,773 A * | 12/1993 | Vidal | 604/342 |
| 5,618,276 A * | 4/1997 | Leise et al. | 604/336 |
| 5,714,225 A | 2/1998 | Hansen et al. | |
| 5,800,415 A | 9/1998 | Olsen | |
| 6,071,268 A | 6/2000 | Wagner | |
| 6,162,456 A * | 12/2000 | Dunbar et al. | 424/448 |
| 6,210,384 B1 * | 4/2001 | Cline | 604/338 |
| 6,332,879 B1 * | 12/2001 | Nielsen et al. | 604/344 |
| 6,679,866 B1 * | 1/2004 | Gunawan | 604/338 |
| 6,764,474 B2 * | 7/2004 | Nielsen et al. | 604/344 |
| 2003/0004477 A1 * | 1/2003 | Nielsen et al. | 604/336 |
| 2004/0073179 A1 * | 4/2004 | Andersen | 604/338 |

FOREIGN PATENT DOCUMENTS

| | | |
|---|---|---|
| WO | 93/18725 | 9/1993 |
| WO | 94/18919 | 9/1994 |
| WO | 98/17212 | 4/1998 |
| WO | 98/53771 | 12/1998 |
| WO | 98/53772 | 12/1998 |
| WO | 98/55057 | 12/1998 |
| WO | 00/49981 | 8/2000 |
| WO | WO 00/67683 A1 * | 11/2000 |

* cited by examiner

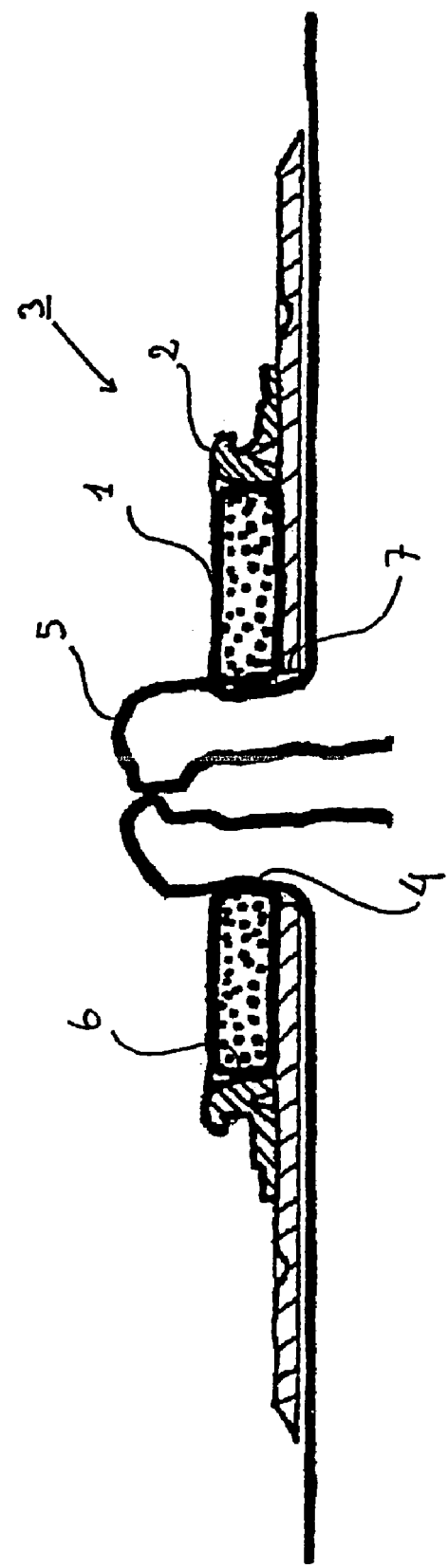

OSTOMY APPLIANCE WITH A REMOVABLE, WASHABLE AND REUSABLE SEALING MEMBER

This is a nationalization of PCT/DK02/00623 filed Sep. 23, 2002 and published in English.

BACKGROUND OF THE INVENTION

1. Field of the Invention

The present invention relates to an ostomy appliance comprising a body side member comprising an adhesive wafer for securing the appliance to a user's skin, said wafer having a hole for receiving a stoma, and a separately exchangeable receiving bag secured to the body side ostomy member for receiving fluids or excretions emerging from an abdominal stoma and a sealing member for sealing between a stoma and an ostomy body side member.

In connection with surgery for a number of diseases in the gastrointestinal or urinary tract a consequence is, in many cases, that the colon, the ileum or the ureter has been exposed surgically and the patient is left with an abdominal stoma, or, in nephrostomy or ureterostomy, the ureter or a catheter is exposed in the back or the chest region or abdominal region, and the effluents or waste products of the body, which are conveyed through these organs, are discharged through the artificial orifice or opening and are collected in a collection bag, which is usually adhered to the skin by means of an adhesive wafer or plate having an inlet opening for accommodating the stoma/ureter/catheter. Also in connection with a fistula, the patient will have to rely on an appliance to collect the bodily material emerging from such opening.

Ostomy appliances are well known. Such appliances may be two-piece or one-piece appliances. In both types of appliances, an adhesive barrier member (or base plate) is attached to the wearer's abdomen/back/chest. In case of a one-piece appliance, a receiving member or bag is attached to the base plate. In case of a two-piece appliance, the adhesive barrier member forms part of a body side member and a receiving member or bag is attached releasably to the body side ostomy member for receiving exudates from the stoma.

When using one-piece appliances, the whole appliance, including the adhesive skin barrier securing the appliance to the skin is normally removed and replaced by a fresh appliance. When using two-piece appliances, the body side ostomy member is left in place up to several days, and only the receiving member or bag attached to the body side member is replaced. The attachment means for attaching an ostomy receiving bag may e.g. be a system se comprising matching coupling rings or matching flanges and adhesive surfaces engaging with and sealing against a flange area of the body side member.

2. Description of the Related Art

Published International Patent Application No. WO 98/17212 discloses an ostomy appliance comprising a body side member comprising an adhesive wafer or pad for securing the appliance to the user's skin, said wafer or pad having a hole for receiving a stoma, and an optionally separately exchangeable receiving member or bag secured to the body side ostomy member for receiving secretions from the ostomy said ostomy appliance further comprising a separate sealing member disposed in the hole of the wafer or pad surrounding the stoma, said sealing member being of a hypo-allergenic adhesive and being in the form of a mouldable mass or a ring.

Published International Patent Application No. WO 00/49981 discloses an ostomy appliance comprising a body side member, an optionally separately exchangeable receiving member or bag secured to the body side member, said body side member comprising a ring-shaped body having an adhesive wafer having a hole for accommodating a stoma and further a separate sealing member is in the form of a disc which, when in use, is placed in the hole for sealing against the stoma, wherein the disc has an outer diameter smaller than the diameter of the hole of the wafer or pad of the ostomy body side member and a flange member stretching from its outer rim, and wherein the flange has outer dimensions greater than the diameter of the hole of the body side member for coupling to the body side member.

Published International Patent Application No. WO 98/53771 also discloses an ostomy appliance comprising a body side member comprising an adhesive wafer or pad for securing the appliance to the user's skin, said wafer or pad having a hole for receiving a stoma, and an optionally separately exchangeable receiving member or bag secured to the body side ostomy member for receiving secretions from the ostomy said ostomy appliance further comprising a sealing member disposed in the hole of the wafer or pad surrounding the stoma wherein the sealing member disposed in the hole of the wafer or pad surrounding the stoma, said sealing member having a hole for accommodating the stoma and said sealing member having balanced plastic and elastic properties allowing an adaptation of the hole of the ostomy appliance to a stoma by a temporary enlarging the hole by everting or rolling up the inner rim of the hole for accommodating the stoma.

Published International Patent Application No. WO 98/53772 discloses an ostomy appliance comprising a body side, member comprising an adhesive wafer or pad for securing the appliance to the user's skin, said wafer or pad having a hole for receiving a stoma, and an separately exchangeable receiving member or bag secured to the body side ostomy member for receiving secretions from the ostomy said ostomy appliance further comprising a separate sealing member disposed in the hole of the wafer or pad surrounding the stoma wherein the separately exchangeable receiving member or bag is secured releasably to the body side ostomy member by a mechanical fastening means.

Although the above references disclose the use of a separate sealing member there is still need of a separate sealing member that may be used together with conventional two-piece ostomy appliances in order to allow an extension of the service time of the body side member for use with an increased number of receiving bags and thus reduce the frequency of stressing the skin around the stoma due to exchange of the body side member by protecting the surface of the adhesive wafer from soiling by and attack from the aggressive visceral contents and facilitating the cleaning of the body side member. Furthermore, there is a need of an improved protecting sealing member improving the safety and quality of life of ostomates having an active social life without having to carry both fresh collecting bags and fresh sealing members while being out of the daily whereabouts.

SUMMARY OF THE INVENTION

The present invention relates to an ostomy appliance comprising a body side member comprising an adhesive wafer for securing the appliance to the user's skin, said wafer having a hole for receiving a stoma, wherein the body side member comprises first substantially annular coupling means for releasable attachment of a separately exchangeable receiving bag to the body side ostomy member for receiving secretions from the stoma, said receiving bag comprising matching second substantially annular coupling means, wherein the body side member comprises a separate sealing member for sealing against the stoma, wherein the separate sealing member is in the form of a disc having a centre hole for accommodating the stoma and wherein at least the surface of the disc facing the skin of the user comprises a mass of a skin-friendly adhesive.

Furthermore, the invention relates to a sealing member for sealing between a stoma and an ostomy body side member comprising an adhesive wafer for securing the appliance to the user's skin, said wafer having a hole for receiving a stoma, wherein the body side member comprises first substantially annular coupling means for releasable attachment of a separately exchangeable receiving bag to the body side ostomy member for receiving secretions from the stoma which sealing member is in the form of a disc having a centre hole for accommodating the stoma and wherein at least the surface of the disc facing the skin of the user comprises a mass of a skin-friendly adhesive.

BRIEF DESCRIPTION OF THE DRAWINGS

The invention is disclosed more in detail with reference to the drawings in which the FIGURE shows a sectional view of an embodiment of the invention in which a sealing disc is placed within the limits of a coupling ring of an ostomy body side member being situated on the user.

DETAILED DESCRIPTION OF THE PRESENT INVENTION

The invention relates to an ostomy appliance comprising a body side member comprising an adhesive wafer for securing the appliance to the user's skin, said wafer having a hole for receiving a stoma, wherein the body side member comprises first substantially annular coupling means for releasable attachment of a separately exchangeable receiving bag to the body side ostomy member for receiving secretions from the stoma, said receiving bag comprising matching second substantially annular coupling means, wherein the body side member comprises a separate sealing member for sealing against the stoma, wherein the separate sealing member is in the form of a disc having a centre hole for accommodating the stoma and wherein at least the surface of the disc facing the skin of the user comprises a mass of a skin-friendly adhesive, wherein the disc has a maximum outer diameter corresponding to the inner diameter of the first annular coupling means and wherein the centre hole of the disc has a diameter smaller than the diameter of the stoma-receiving hole of the body side member ensuring that the disc covers all of the surface of the adhesive wafer facing away from the user located between the first annular coupling means and the stoma, said disc being made from a material that may be detached, rinsed and reapplied.

It has been found that an ostomy appliance of the invention fulfils the above needs and also provides further advantages as appears from the below. The sealing member of the invention protects the body side member against contact with and attack by the aggressive visceral contents and has a service time at least corresponding to and even exceeding the service time of the body side member. Thus, it better protects the body side member from soiling and also eases the cleaning thereof using water when substituting the receiving bag. This also renders it possible to extend the service time of the sealing member to cover at least the service time of the body side member and several changes of collecting bag. Thus, when changing bag while being out of the daily whereabouts, the ostomate may reuse the sealing member and thus does not have to carry both fresh collecting bags and fresh sealing members.

As the outer diameter of the disc corresponds to the inner diameter of the coupling means, the adaptation of the hole of the body side member to the stoma is less critical as the disc covers all of the surface of the body side member inside the coupling means and thus protects the surface of the body side member from contact with visceral contents reducing the need of cleaning when substituting the collection bag with a fresh. This also enables the option of using body side members having a large hole generally and to avoid the individual adaptation of the size of the hole in most cases. Furthermore, only a relatively few number of sizes of sealing members of the invention, corresponding to the number of sizes of coupling rings, are needed, which sealing members furthermore only have to be adapted with respect to the size of the centre hole in order to provide a safe sealing which simplifies the use of the sealing members.

It is preferred that the diameter of the centre hole of the sealing member corresponds to the diameter of the stoma which ensures a complete protection of the body side member as well as of the skin surrounding the stoma.

In one embodiment of the invention the coupling means is in the form of matching flanges and adhesive surfaces.

In a preferred embodiment of the invention the annular coupling means is in the form of matching coupling rings.

In accordance with a further preferred embodiment of the invention, the thickness of the sealing member is of the same size as the distance between the surface of the adhesive wafer facing away from the user and the top of the coupling ring or the flange as the sealing member then covers and protects the full surface of the first coupling means facing the stoma and thus reduces the risk of soiling of parts of the body side member and consequently also reduces the necessary cleaning.

It is preferred that the whole disc is made from an adhesive being resistant to attack from visceral contents as it is supposed to be in service for extended periods of time.

In order to facilitate cleaning of the body side member when substituting receiving bags it is preferred that the skin-friendly adhesive is suitable for repeated adhering to and removal from the skin. Thus, the sealing member may be removed from the body side member and cleaned and repositioned and used for further protection of the body side member. It is especially preferred that the skin-friendly adhesive is made from a permanently tacky silicone adhesive as such material may be cleaned using water and does not bind materials or odour emerging from a stoma. Thus a clean environment is easy to maintain.

In accordance with a preferred embodiment the surface of the disc facing away from the user is covered with a non-tacky layer in order to reduce the risk of adherence of materials emerging from a stoma or the opposite bag wall if it is brought in contact with the disc by accident.

One practical solution is obtained when the surface facing away from the user is covered with a non-tacky polymer film, e.g. a film of a polyolefin such as polyethylene or polypropylene or a silicone polymer.

The disc is preferably made from a silicone material as silicone materials are generally skin-friendly and very stable when contacted by aggressive exudates from a stoma and furthermore, silicones may be cleaned by rinsing with water without having to rely on the use of detergents which further facilitates repeated cleaning and use of a sealing member. Furthermore, silicones are often transparent enabling an inspection of the area around the stoma without having to remove the sealing disc which reduces the stress of the skin connected with removal and replacing the sealing disc. Still further, when producing sealing members from silicones, it is not necessary to rely on protecting or containment sheet materials.

A preferred material for the non-tacky layer is a silicone rubber being relatively inert for aggressive fluids and being washable using water. Suitable materials are platinum catalysed vinyl endblocked polydiorganosiloxanes of the kind described in U.S. Pat. No. 3,983,298, which have high tack, good adhesive strength. The properties and tack of these polysiloxanes may be adjusted according to wish by routine experiments by the skilled in the art for preparation of more tacky materials for adhering to the skin and less tacky or non-tacky layers for the surface facing away from the user. A preferred material is vinyl endblocked crosslinked polydimethylsiloxanes. Furthermore, it is preferred that the surface of the disc facing away from the user is hydrophobic as this facilitates the cleansing thereof.

The sealing member used in accordance with the invention may be elastic enabling a temporary enlargement of the hole for receiving the stoma whereafter the disc reverts to substantially its original shape as long as the elastic force is not so strong that there is a risk of constricting the stoma. Its is also considered an embodiment of the invention that the sealing member is plastically mouldable allowing a final adaptation of the shape thereof to fit more snugly to the stoma.

It is also contemplated that the sealing member used in accordance with the invention is somewhat plastic allowing for a minor displacement of material to allow a full engagement with the surface of the stoma.

It is preferred that the material is slightly conformable and adapts itself to the actual surface of the stoma. This active adaptation is more efficient when the sealing member is of a thickness corresponding to the height of a coupling ring.

The choice of materials having the above-referenced properties may made by the skilled in the art based on routine experiments.

An ostomy body side member according to the invention may be produced from standard materials normally used for preparation of disposable ostomy and wound and incontinence devices. Thus, the carrier sheet may be any suitable thermoplastic material and the adhesive wafer may be made from a medical grade barrier adhesives known in the such as the formulation being disclosed, for example in U.S. Pat. Nos. 4,367,732, 5,051,259 or 5,714,225.

The coupling means-may be any system known per se for attaching receiving bags to ostomy body side members and may suitably be matching coupling rings of the type disclosed in WO 93/18725 or WO 94/18919 or matching flanges for adhesive connection of the type disclosed in U.S. Pat. No. 5,800,415.

In a further aspect the invention relates to a sealing member for sealing between a stoma and an ostomy body side member comprising an adhesive wafer for securing the appliance to the user's skin, said wafer having a hole for receiving a stoma, wherein the body side member comprises first substantially annular coupling means for releasable attachment of a separately exchangeable receiving bag to the body side ostomy member for receiving secretions from the stoma which sealing member is in the form of a disc having a hole for accommodating the stoma and wherein at least the surface of the disc facing the skin of the user comprises a mass of a skin-friendly adhesive wherein the disc has a maximum outer diameter corresponding to the inner diameter of the first annular coupling means and wherein the centre hole of the disc has a diameter smaller than the diameter of the stoma-receiving hole of the body side member with which it is intended to be used.

DESCRIPTION OF THE PREFERRED EMBODIMENTS

The invention is now explained more in detail with reference to the drawings showing preferred embodiments of the invention. However, it should be understood that the detailed description and specific example, while indicating a preferred embodiment of the invention, are given by way of illustration only, since various changes and modifications within the spirit and scope of the invention will become apparent to those skilled in the art from this detailed description.

Reference is made to the FIGURE of the drawings showing a sectional view of an embodiment of an ostomy body side member of the invention in which a sealing disc 1 is placed within the limits of a coupling ring 2 of the body side member 3 being situated on the user. As appears, the disc has an opening 4 for receiving a stoma 5 and fills out the space between the stoma 5 the coupling, ring 2 for releasable attachment of a receiving bag. Thus, the disc has an outer diameter corresponding to the inner diameter of the coupling ring so that the disc and the coupling ring are in sealing contacting in the interface 6 and the diameter of the centre hole or opening 4 is smaller than the diameter of the stoma-receiving hole 7 of the body side member.

As also appears, the sealing disc 1 protects all of the surface of the body side member facing away from the user from direct contact with material exiting the stoma and thus from soiling or attack from such material.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. An ostomy appliance comprising a body side member including an adhesive wafer for securing the appliance to a user's skin, said wafer having a hole for receiving a stoma, said body side member including a first substantially annular coupling element for releasable attachment of a separately exchangeable receiving bag to the body side ostomy member for receiving secretions from the stoma, said receiving bag having a matching second substantially annular coupling element, a separate sealing member for sealing against the stoma, said separate sealing member being in the form of a disc having a centre hole for accommodating the stoma, at least the surface of the disc facing the skin of the user including a mass of a skin-friendly adhesive, said disc having a maximum outer diameter corresponding to the inner diameter of the first annular coupling element and the centre hole of the disc having a diameter smaller than the diameter of the stoma-receiving hole of the body side member ensuring that the disc covers all of the surface of the adhesive wafer facing away from the user located between the first annular coupling element and the stoma, said disc being made from a material that enables said disc to be detached, rinsed with water without detergents and reapplied to the body side member for reuse thereof in sealing against said stoma.

2. The ostomy appliance as claimed in claim 1 wherein the diameter of the centre hole of the sealing member corresponds to the diameter of the stoma.

3. The ostomy appliance as claimed in claim 1 wherein the annular coupling element is in the form of matching flanges and adhesive surfaces.

4. The ostomy appliance as claimed in claim 1 wherein the annular coupling means is in the form of matching coupling rings.

5. The ostomy appliance as claimed in claim 4 wherein the thickness of the sealing member is of the same size as the distance between the surface of the adhesive wafer facing away from the user and the top of the coupling ring.

6. The ostomy appliance as claimed in claim 1 wherein the sealing member is made from an adhesive being resistant to attack from visceral contents.

7. The ostomy appliance as claimed in claim 6 wherein the sealing member is made from a skin-friendly adhesive being suitable for repeated adhering to and removal from the skin.

8. The ostomy appliance as claimed in claim 7 wherein the skin-friendly adhesive is made from a permanently tacky silicone adhesive.

9. The ostomy appliance as claimed in claim 6 wherein the surface of the disc facing away from the user is covered with a non-tacky layer.

10. The ostomy appliance as claimed in claim 9 wherein the the non-tacky layer is a polymer film.

11. The ostomy appliance as claimed in claim 9 wherein the non-tacky layer is a silicone rubber.

12. The ostomy appliance as claimed in claim 1, wherein the surface of the disc facing away from the user is hydrophobic.

13. The ostomy appliance as claimed in claim 1, wherein the sealing member is elastic.

14. The combination as claimed in claim 1, wherein the sealing member is elastic.

15. A separately exchangeable sealing member in combination with an ostomy body side member comprising an adhesive wafer for securing the appliance to the user's skin, said wafer having a hole for receiving a stoma, said body side member having a substantially annular coupling element for releasable attachment of a separately exchangeable receiving bag to the body side ostomy member for receiving secretions from the stoma, said sealing member being in the form of a disc having a centre hole for accommodating the stoma, at least the surface of the disc facing the skin of the user including a mass of a skin-friendly adhesive, said disc having a maximum outer diameter corresponding to the inner diameter of the first annular coupling element and the centre hole of the disc having a diameter smaller than the diameter of the stoma-receiving hole of the body side member with which the sealing member is intended to be used, said disc being made from a material that enables said disc to be detached, rinsed with water without detergents and reapplied to the body side member for reuse thereof in sealing against said stoma.

16. The combination as claimed in claim 15, wherein the surface of the disc facing away from the user is hydrophobic.

* * * * *